(12) United States Patent
Fumiyama et al.

(10) Patent No.: US 10,058,656 B2
(45) Date of Patent: Aug. 28, 2018

(54) SYRINGE WITH ROTATABLE ELEMENT, SYSTEMS INCLUDING THE SYRINGE, AND ASSOCIATED METHODS

(75) Inventors: Hideo Fumiyama, Tokyo (JP); Shawn P. Fojtik, Park City, UT (US)

(73) Assignee: PMT Partners, LLC, Park City, UT (US)

( * ) Notice: Subject to any disclaimer, the term of this patent is extended or adjusted under 35 U.S.C. 154(b) by 1149 days.

(21) Appl. No.: 11/877,564

(22) Filed: Oct. 23, 2007

(65) Prior Publication Data

US 2008/0132850 A1 Jun. 5, 2008

Related U.S. Application Data

(60) Provisional application No. 60/853,817, filed on Oct. 24, 2006.

(51) Int. Cl.
*A61M 5/31* (2006.01)
(52) U.S. Cl.
CPC ......... *A61M 5/3129* (2013.01); *A61M 5/3135* (2013.01); *A61M 2005/3139* (2013.01)
(58) Field of Classification Search
CPC ........ A61M 5/24; A61M 5/28; A61M 5/3129; A61M 5/31511; A61B 10/0283
USPC ........ 604/181, 187, 207, 208, 210, 227, 223
See application file for complete search history.

(56) References Cited

U.S. PATENT DOCUMENTS

| 530,187 A | 12/1894 | Lasky |
|---|---|---|
| 870,573 A | 11/1907 | Myers |
| 901,567 A | 10/1908 | Utschig |
| 1,019,207 A | 3/1912 | Ward |
| 1,218,513 A | 3/1917 | Biron |
| 1,331,805 A | 2/1920 | Chance |
| 1,718,596 A | 8/1927 | Smith |
| 2,532,598 A | 12/1950 | Boeger |

(Continued)

FOREIGN PATENT DOCUMENTS

| DE | 19647529 A1 | 5/1998 |
|---|---|---|
| DE | 19732332 A1 | 2/1999 |

(Continued)

OTHER PUBLICATIONS

Supplementary Partial European Search Report in European Application No. EP 08 78 0563.6 dated Jan. 15, 2015.

(Continued)

*Primary Examiner* — Bhisma Mehta
*Assistant Examiner* — Matthew A Engel
(74) *Attorney, Agent, or Firm* — Durham Jones & Pinegar, PC., Intellectual Property Law Group

(57) ABSTRACT

A syringe includes a barrel and a rotatable element on the barrel; for example at a proximal location along the length of the barrel. The rotatable element rotates at least partially around the barrel. When a handle is associated with the rotatable element, the barrel may rotate as the handle his held substantially stationary or the handle may be rotated while the barrel and any peripheral device secured thereto remain substantially stationary. When handles are associated with a rotatable element that may be removed from a barrel, a barrel that is disassembled from the rotatable element may be replaced with another barrel of the same or a different configuration. Methods of using a syringe with a rotatable element on a barrel thereof are also disclosed.

23 Claims, 4 Drawing Sheets

(56) References Cited

U.S. PATENT DOCUMENTS

| | | | |
|---|---|---|---|
| 2,748,767 A | 6/1956 | Wright | |
| 2,904,043 A * | 9/1959 | Friedman | 604/228 |
| 3,016,897 A | 1/1962 | Kendrick | |
| 3,110,310 A * | 11/1963 | Cislak | 604/209 |
| 3,150,801 A * | 9/1964 | Hamilton | 222/158 |
| 3,212,685 A | 10/1965 | Swan et al. | |
| 3,281,023 A * | 10/1966 | Bruck et al. | 222/390 |
| 3,770,169 A | 11/1973 | Roach | |
| 3,840,007 A | 10/1974 | Fish | |
| 4,020,838 A | 5/1977 | Phillips et al. | |
| 4,187,849 A | 2/1980 | Stim | |
| 4,204,539 A | 5/1980 | Van Brugge | |
| 4,330,070 A | 5/1982 | Doubleday | |
| 4,368,731 A | 1/1983 | Schramm | |
| 4,425,121 A | 1/1984 | Young et al. | |
| RE32,214 E | 7/1986 | Schramm | |
| 4,712,545 A | 12/1987 | Honkanen | |
| 4,738,664 A | 4/1988 | Prindle | |
| 4,744,789 A | 5/1988 | Johnson | |
| 4,808,165 A | 2/1989 | Carr | |
| 4,832,692 A | 5/1989 | Box et al. | |
| 4,861,339 A | 8/1989 | Jonischkeit | |
| 4,917,679 A * | 4/1990 | Kronner | 604/198 |
| 4,923,096 A | 5/1990 | Ennis, III | |
| 4,968,303 A | 11/1990 | Clark et al. | |
| 4,994,065 A | 2/1991 | Gibbs et al. | |
| 5,027,605 A | 7/1991 | Hardesty | |
| 5,037,399 A | 8/1991 | Reichert et al. | |
| 5,045,066 A * | 9/1991 | Scheuble et al. | 604/198 |
| 5,069,421 A | 12/1991 | Kishi et al. | |
| 5,078,690 A | 1/1992 | Ryan | |
| 5,112,307 A | 5/1992 | Haber et al. | |
| 5,133,483 A | 7/1992 | Buckles | |
| 5,135,507 A | 8/1992 | Haber et al. | |
| 5,139,488 A | 8/1992 | Klein | |
| 5,150,488 A | 9/1992 | Yuan et al. | |
| 5,176,647 A | 1/1993 | Knoepfler | |
| 5,188,610 A | 2/1993 | Rains | |
| 5,213,115 A | 5/1993 | Zytkovicz et al. | |
| 5,228,883 A | 7/1993 | Blakely et al. | |
| 5,288,285 A | 2/1994 | Carter | |
| 5,279,563 A | 4/1994 | Brucker et al. | |
| 5,304,147 A | 4/1994 | Johnson et al. | |
| 5,306,147 A | 4/1994 | Dragan et al. | |
| 5,308,358 A | 5/1994 | Bond et al. | |
| 5,336,201 A | 8/1994 | von der Decken | |
| 5,350,365 A | 9/1994 | De Godoy Moreira | |
| 5,368,202 A | 11/1994 | Smrt | |
| 5,419,775 A | 5/1995 | Haffner et al. | |
| 5,425,743 A | 6/1995 | Nicholas | |
| 5,453,093 A * | 9/1995 | Haining | 604/110 |
| 5,480,409 A | 1/1996 | Riza | |
| 5,499,998 A | 3/1996 | Meade | |
| 5,505,704 A | 4/1996 | Pawelka et al. | |
| 5,507,727 A | 4/1996 | Crainich | |
| 5,507,730 A | 4/1996 | Haber et al. | |
| 5,511,556 A | 4/1996 | DeSantis | |
| 5,531,708 A | 7/1996 | Woodruff | |
| 5,560,373 A | 10/1996 | DeSantis | |
| 5,562,655 A | 10/1996 | Mittelstadt et al. | |
| 5,591,135 A | 1/1997 | Sullivan | |
| 5,591,176 A | 1/1997 | Henderson et al. | |
| 5,645,561 A | 7/1997 | Smith et al. | |
| 5,692,642 A | 12/1997 | Brattesani | |
| 5,722,829 A | 3/1998 | Wilcox et al. | |
| 5,733,258 A * | 3/1998 | Lane | 604/506 |
| 5,735,874 A | 4/1998 | Measamer et al. | |
| 5,749,968 A | 5/1998 | Melanson et al. | |
| 5,755,362 A | 5/1998 | Rodriguez, Jr. et al. | |
| 5,807,340 A | 9/1998 | Pokras | |
| 5,830,194 A | 11/1998 | Anwar et al. | |
| 5,851,214 A | 12/1998 | Larsen et al. | |
| 5,867,911 A | 2/1999 | Yates et al. | |
| 5,881,928 A | 3/1999 | Register et al. | |
| 5,893,488 A | 4/1999 | Hoag et al. | |
| 5,951,517 A | 9/1999 | Lampropoulos et al. | |
| 5,961,494 A | 10/1999 | Hogan | |
| 5,961,496 A | 10/1999 | Nielsen et al. | |
| 5,964,380 A | 10/1999 | Hazzard et al. | |
| 5,964,736 A | 10/1999 | Lane | |
| 5,992,694 A | 11/1999 | Keller | |
| 6,007,515 A | 12/1999 | Epstein et al. | |
| 6,024,728 A | 2/2000 | Schulz | |
| 6,030,368 A | 2/2000 | Anwar et al. | |
| 6,047,861 A | 4/2000 | Vidal et al. | |
| 6,080,136 A | 6/2000 | Trull et al. | |
| 6,117,158 A | 9/2000 | Measamer et al. | |
| 6,183,444 B1 | 2/2001 | Glines et al. | |
| 6,213,984 B1 | 4/2001 | Lane et al. | |
| 6,241,708 B1 | 6/2001 | Reilly et al. | |
| 6,264,637 B1 | 7/2001 | Hogan | |
| 6,368,307 B1 | 4/2002 | Ziemba et al. | |
| 6,406,460 B1 | 6/2002 | Hogan | |
| 6,439,439 B1 | 8/2002 | Rickard et al. | |
| 6,585,696 B2 | 7/2003 | Petersen et al. | |
| 6,607,512 B2 | 8/2003 | Oliver et al. | |
| 6,752,781 B2 | 6/2004 | Landau et al. | |
| 6,764,466 B1 | 7/2004 | Staats et al. | |
| 6,802,824 B2 | 10/2004 | Mickley et al. | |
| 7,041,084 B2 | 5/2006 | Fojtik | |
| 7,097,636 B2 | 8/2006 | Pessin | |
| 7,125,395 B2 | 10/2006 | Hommann et al. | |
| 7,988,677 B2 | 8/2011 | Fojtik | |
| 8,021,333 B2 | 9/2011 | Kaal et al. | |
| 8,672,893 B2 | 3/2014 | Fojtik | |
| 2002/0022805 A1 | 2/2002 | Lane | |
| 2002/0183698 A1 | 12/2002 | Quinn et al. | |
| 2003/0139706 A1 | 7/2003 | Gray | |
| 2003/0187400 A1 | 10/2003 | Liao | |
| 2003/0195492 A1 | 10/2003 | Gobron et al. | |
| 2004/0116873 A1 | 6/2004 | Fojtik | |
| 2004/0116893 A1 | 6/2004 | Spohn et al. | |
| 2004/0164097 A1 | 8/2004 | Orecchia et al. | |
| 2004/0210200 A1 | 10/2004 | Gerondale et al. | |
| 2005/0070848 A1 | 3/2005 | Kim et al. | |
| 2005/0070912 A1 | 3/2005 | Voellmicke | |
| 2005/0137575 A1 | 6/2005 | Thompson et al. | |
| 2006/0247578 A1 | 11/2006 | Arguedas et al. | |
| 2007/0010788 A1 | 1/2007 | Evans | |
| 2007/0106226 A1 | 5/2007 | Croll et al. | |
| 2007/0265573 A1 | 11/2007 | Fojtik | |
| 2008/0004703 A1 | 1/2008 | Trieu et al. | |
| 2010/0217122 A1 | 8/2010 | Fumiyama et al. | |
| 2011/0008750 A1 | 1/2011 | Dillard, III | |
| 2014/0200483 A1 | 7/2014 | Fojtik | |

FOREIGN PATENT DOCUMENTS

| | | |
|---|---|---|
| EP | 0474218 A1 | 3/1992 |
| EP | 0565045 A1 | 10/1993 |
| EP | 0919251 B1 | 6/1999 |
| EP | 1066797 B1 | 1/2001 |
| EP | 1148834 B1 | 10/2001 |
| EP | 1301227 B1 | 4/2003 |
| EP | 1440706 A1 | 7/2004 |
| FR | 2 009 514 | 2/1970 |
| FR | 2207728 | 6/1974 |
| FR | 20 683 140 | 5/1993 |
| WO | 9908735 A2 | 2/1999 |
| WO | 02094343 A2 | 11/2002 |
| WO | 04062713 A1 | 7/2004 |
| WO | 2007133615 | 11/2007 |

OTHER PUBLICATIONS

Japanese Patent Office, "Notice of Reason for Rejection," dated Mar. 30, 2015, in Japanese patent application No. 2014-147359.
United States Patent and Trademark Office Acting as the International Searching Authority, "International Search Report and Writ-

(56) References Cited

OTHER PUBLICATIONS ten Opinion," dated Dec. 28, 2015, in international application No. PCT/US2015/052506.

* cited by examiner

SYRINGE WITH ROTATABLE ELEMENT, SYSTEMS INCLUDING THE SYRINGE, AND ASSOCIATED METHODS

CROSS-REFERENCE TO RELATED APPLICATION

This application claims the benefit of priority under 35 U.S.C. § 119(e) to U.S. Provisional Application No. 60/853,817, filed Oct. 24, 2006, the disclosure of which is hereby incorporated herein, in its entirety, by this reference.

FIELD

The present invention relates generally to syringes and, more specifically, to syringes with circumferentially rotatable elements on the barrels thereof. The present invention also relates to infusion and/or aspiration systems that include syringes with rotatable elements, as well as to methods for using such syringes.

SUMMARY

In one aspect, the present invention includes syringes with slip rings. An embodiment of such a syringe includes a syringe barrel with a ring or other rotatable element concentrically disposed about a section of the barrel. As an example, the rotatable element may be disposed at or near a proximal end of the barrel (i.e., the end into which a plunger is introduced). The rotatable element is configured to rotate relative to the barrel. In some embodiments, at least a portion of the rotatable element is captured within a groove that extends circumferentially around a section of the barrel. In other embodiments, one or more features that protrude (e.g., a lip, a series of aligned protrusions, etc.) circumferentially from the barrel of the syringe engage a groove formed in an inner surface of the rotatable element.

According to another aspect of the present invention, a syringe barrel with a slip ring may be used as part of a more complex syringe, such as a control syringe or a leveraged syringe (e.g., a syringe with leveraged handles). In a complex syringe of this type, the rotatable element may be secured to a handle that is typically held during use of the syringe, while the barrel of the syringe is free to rotate relative to the orientation in which the handle is held.

In a further aspect, an infusion or aspiration system that includes a syringe with a rotatable element and an infusion or aspiration element, such as a catheter, needle, or the like, secured to a distal end of the barrel. In use, the barrel may rotate relative to a handle that has been secured thereto (e.g., in coupling the barrel to a peripheral device, such as a catheter or needle), or the handle may rotate relative to the barrel (e.g., in use of the syringe while the barrel is coupled to a peripheral device). Such a feature eliminates the need for costly rotatable connections between the syringe barrel and the infusion or aspiration element.

Other features and advantages of the present invention will become apparent to those of ordinary skill in the art through consideration of the ensuing description, the accompanying drawings, and the appended claims.

BRIEF DESCRIPTION OF THE DRAWINGS

In the drawings, which depict features of various aspects of the present invention.

DETAILED DESCRIPTION

Figure 1:
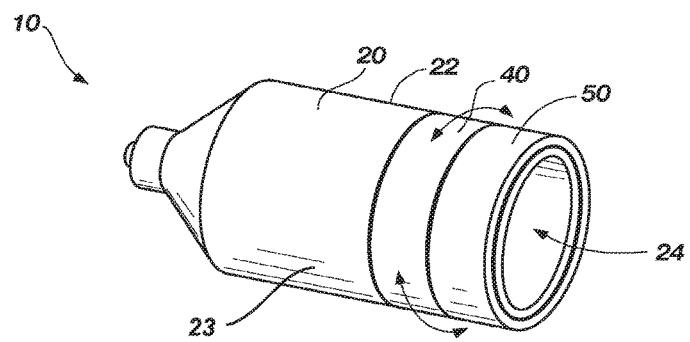
FIG. 1 is a perspective view of an embodiment of syringe according to the present invention, which includes a rotatable element around a portion of a syringe barrel.
Figure 2:
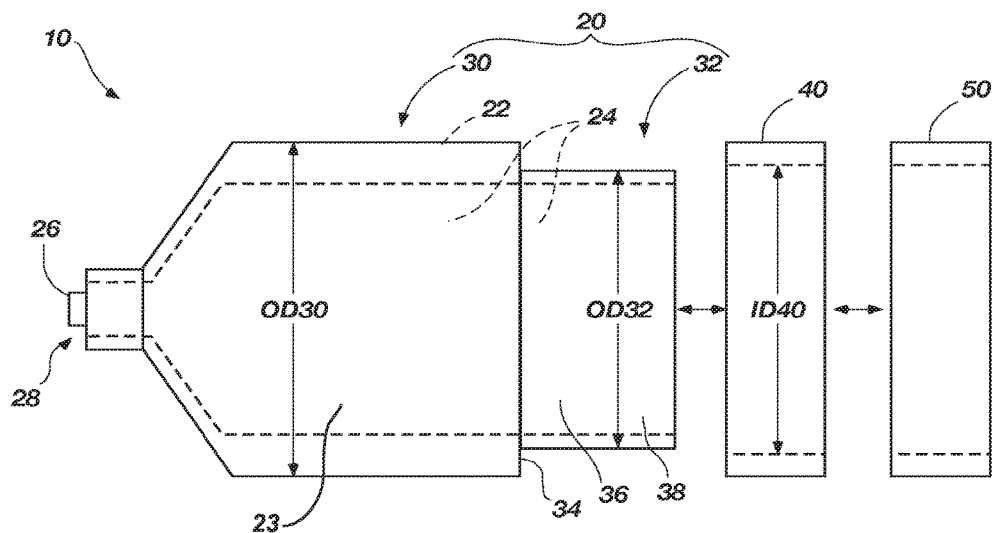
FIG. 2 is a side assembly view of the embodiment of the syringe shown in FIG. 1.
Figure 3:
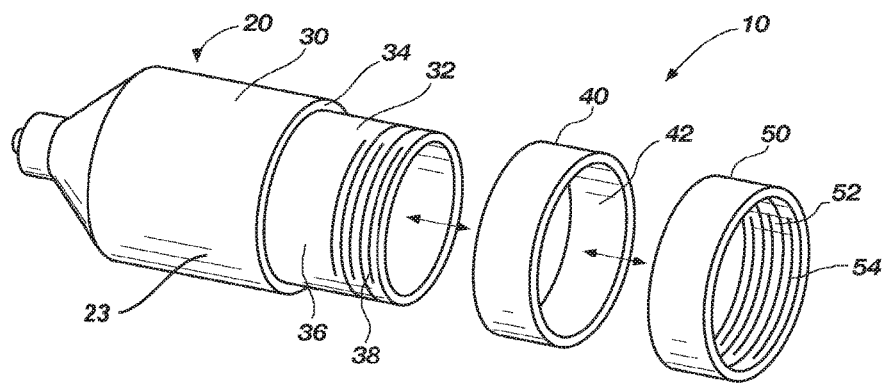
FIG. 3 is a perspective assembly view of the embodiment of the syringe shown in FIG. 1.

With reference to FIGS. 1 through 3, an embodiment of syringe 10 with a barrel 20 and a rotatable element 40 that spins about a circumference of the barrel 20 is depicted. Barrel 20 includes an outer wall 22 that defines an outer surface 23 of barrel 20, as well as a receptacle 24 that extends axially through barrel 20.

A main body 30 of barrel 20, including a central portion of barrel 20, has a substantially uniform outer diameter OD30. At its distal tip 26, outer wall 22 tapers to a much smaller outer diameter, which may form a standard coupling element 28, which may be coupled to an injection or aspiration needle (e.g., a hypodermic needle, biopsy needle, etc.), a catheter, or the like. A proximal end 32 of barrel 20 may also have a substantially uniform outer diameter OD32 but, as shown, its outer diameter OD32 may be smaller than outer diameter OD30 of main body 30, such that a proximal ridge 34 at a boundary between main body 30 and proximal end 32.

In the illustrated embodiment, proximal end 32 includes a distally located axle 36, which may have a substantially smooth surface, and a proximally located retention feature 38. As shown, retention feature 38 may comprise threads or other similar engagement features that are configured to receive, engage, and retain a separate locking element 50, an example of which is provided in further detail below.

Rotatable element 40, which may be annular in shape (i.e., ring-shaped), has a substantially constant inner diameter ID40 that is slightly larger than the outer diameter OD32 of proximal end 32 of barrel 20 but smaller than the outer diameter OD30 of main body 30 of barrel 20, allowing rotatable element 40 to be concentrically placed on proximal end 32. More specifically, rotatable element 40 may be placed over axle 36, adjacent to ridge 34. An inner surface 42 of rotatable element 40 may be substantially smooth. Smoothness of one or both of inner surface 42 and axle 36 may facilitate the free rotation of rotatable element 40 at least partially around axle 36.

As noted, syringe 10 may also include a locking element 50. Locking element 50 may have an inner surface 52 with an engagement feature 54 (e.g., the illustrated threads, etc.) that cooperates with a complementary engagement feature of retention feature 38 at proximal end 32 of barrel 20. When locking element 50 is disposed on retention feature 38, an outer surface of axle 36 is circumferentially recessed relative to outer surfaces of main body 30 of barrel 20 and locking element 50; i.e., a circumferential groove 56 (see FIG. 7) is formed between main body 30 and locking element 50. The dimensions (e.g., a depth) of the resulting groove 56 axially retain rotatable element 40 over axle 36.

Figure 4:
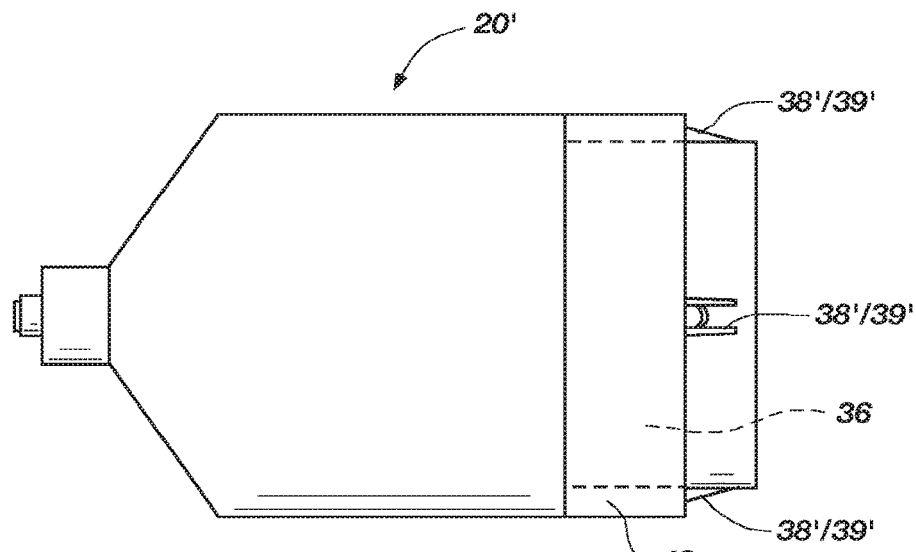
FIG. 4 is a side assembly view of another embodiment of syringe that incorporates teachings of the present invention.

As an alternative to embodiments that include locking elements 50 that are configured for assembly with a retention feature 38 of a barrel 20 of a syringe 10, another embodiment of barrel 20' may include a retention feature 38', as shown in FIG. 4, may facilitate the assembly of a rotatable element 40 with barrel 20', but prevent its removal from barrel 20'. For example, retention feature 38' may include tabs 39' that are configured and oriented to facilitate the placement of rotatable element 40 over axle 36, but prevent rotatable element 40 from being removed from axle 36'. In a more specific embodiment, tabs 39' may be oriented and configured to protrude somewhat from an outer surface of the remainder of retention feature 38'. When rotatable element 40 is positioned on retention feature 38' and slid distally toward axle 36', tabs 39' may be pressed radially inward, allowing rotatable element 40 to slide thereover and onto axle 36'. Once rotatable element 40 has been positioned properly upon axle 36', tabs 39' resiliently rebound to their relaxed state, in which they protrude radially from the surface of the remainder of retention feature 38' and retain rotatable element 40 in place on axle 36'.

Figure 5:
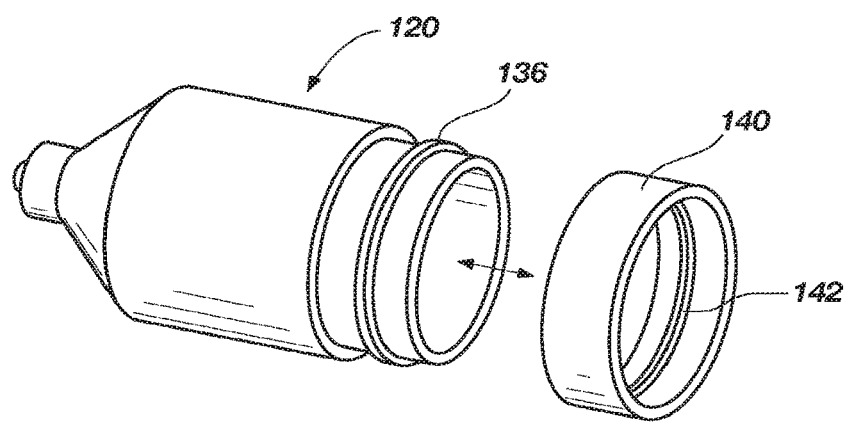
FIG. 5 is a perspective assembly view of an embodiment of syringe with a circumferentially protruding guide for retaining a rotatable element.

FIG. 5 shows another embodiment of barrel 120, which includes one or more protrusions 136 (e.g., a single fillet or ridge, a plurality of aligned protrusions, etc.) that extend circumferentially about a portion of barrel 120. A rotatable element 140 that is configured for assembly with barrel 120 may have a somewhat annular shape and include a groove 142 for receiving protrusion(s) 136. Groove 142 and protrusion(s) 136 are configured to enable rotatable element 140 to rotate at least partially around barrel 120. Protrusion(s) 136 may be configured to facilitate the assembly of rotatable element 140 with barrel 120 while preventing the disassembly of rotatable element 140 from barrel 120. Alternatively, rotatable element 140 may be configured (e.g., with appropriate positioned slots, a hinge and locking element, etc.) to facilitate its placement over and retention by protrusion(s) 136.

Figure 6:
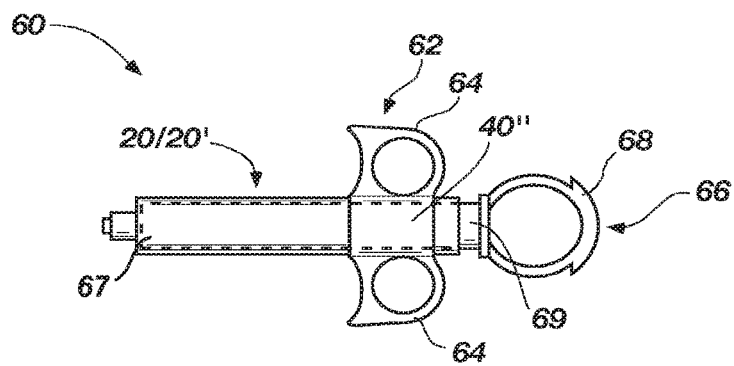
FIG. 6 is a perspective view of an embodiment of syringe barrel with control syringe finger rings on a rotatable element.

Turning now to FIG. 6, an embodiment of a control syringe 60 according to the present invention includes a barrel 20, 20' and a rotatable element 40" with finger loops 64 that protrude therefrom to form a handle 62. Barrel 20, 20' is particularly useful with a plunger 66 that includes a thumb loop 68 at its proximal end. As those of ordinary skill in the art will appreciate, plunger 66 also includes a distal end 67 capable of being introduced into, residing within, and traveling longitudinally through receptacle 24, 24' of barrel 20, 20'.

Figure 7:
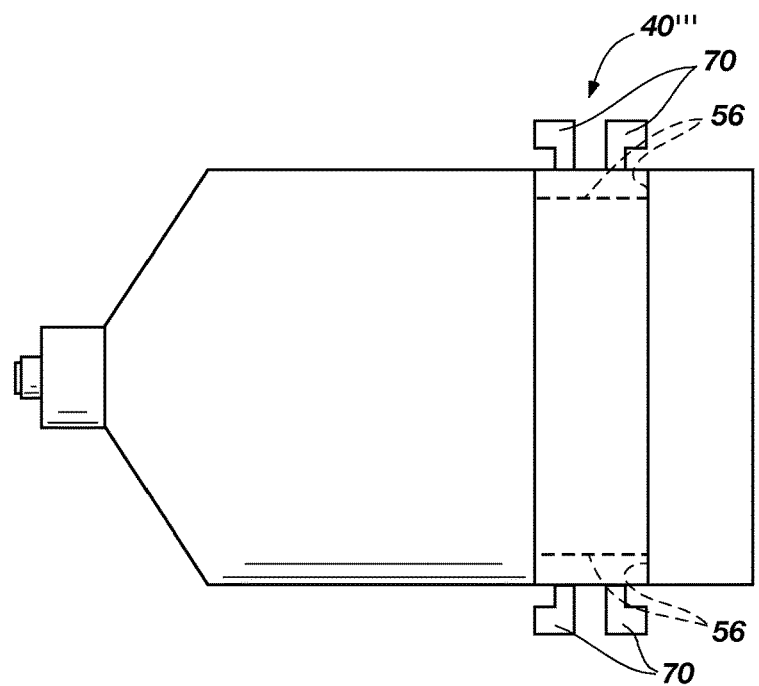
FIG. 7 is a top view of an embodiment of syringe barrel with hinge elements protruding from a rotatable element.

Another variation of rotatable element 40'" is shown in FIG. 7. Rotatable element 40'" includes means for coupling to a handle, such as the depicted hinge elements 70. As depicted, hinge elements 70 may protrude from opposite sides of rotatable element 40'". The axis of rotation of hinge elements 70 may intersect a central axis through rotatable element 40'". With such an arrangement, when rotatable element 40'" is in place over an axle 36 (FIGS. 1 through 4) of a syringe barrel 20, 20' (FIG. 6), the central axis through rotatable element 40'" will substantially align with a central axis through the length of barrel 20, 20'. Thus, in such an arrangement, the axis of rotation of hinge elements 70 will also intersect the central axis through barrel 20, 20'.

Figure 8:
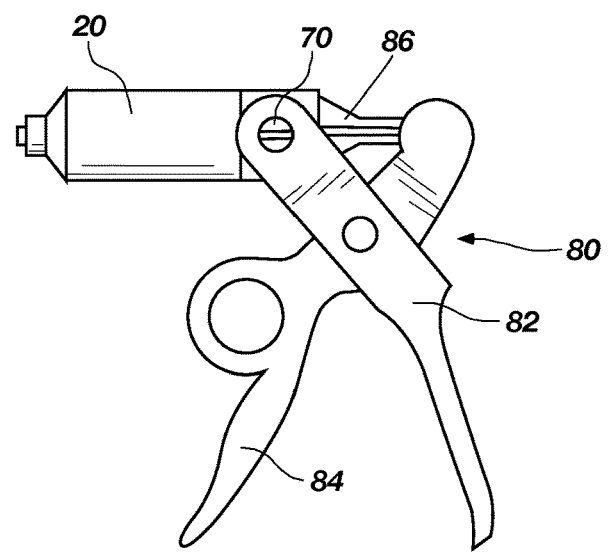
FIG. 8 is a side view of a syringe with a member of pliers-grip handles coupled to the hinge elements shown in FIG. 7.

Hinge elements 70 of the variation of rotatable element 40'" shown in FIG. 7 may facilitate pivotal assembly of rotatable element 40'" with a member 82 of syringe actuation handle 80, such as that shown in FIG. 8. Member 82 of syringe actuation handle 80 is pivotally associated with another member 84 that is coupled to a syringe plunger 86. Nonlimiting examples of such syringe actuation handles are described in U.S. Pat. No. 7,041,084, in U.S. Patent Application Publication US-2006-0270996-A1, in U.S. patent application Ser. No. 11/431,420, filed May 8, 2006, and in U.S. Provisional Patent Application Ser. No. 60/853,878, filed Oct. 24, 2006, the entire disclosure of each of which is, by this reference, hereby incorporated herein.

As noted previously, in some embodiments, rotatable element 40", 40'" may be disassembled from barrel 20 (see, e.g., the embodiment of rotatable element 40 shown in FIGS. 1 through 3). In such embodiments, once a barrel 20 has been used, it may be removed from rotatable element 40", 40'", disposed of, and replaced with a different barrel 20a. Thus, the handles (e.g., handle 62 (FIG. 6) or handles 80 (FIG. 8)) that are associated with such a rotatable element 40", 40'" may be reused, which may reduce the expenses that have conventionally been incurred when many types of syringes, including, but not limited to, control and leveraged syringes, are used.

Figure 9:
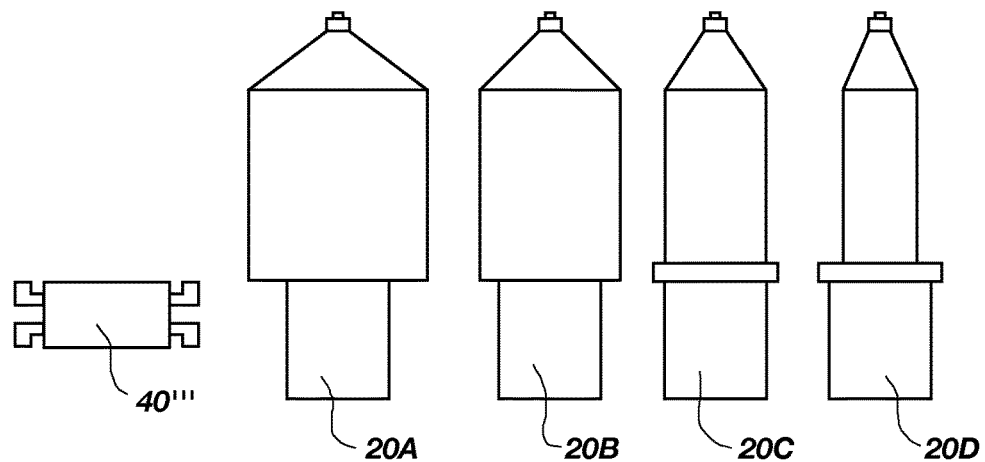
FIG. 9 schematically illustrates a system including handles that are configured to be used with a variety of different barrel configurations.

By enabling barrel replacement, the use of a rotatable element of the present invention (e.g., rotatable element 40", 40'", etc.) in conjunction with reusable handles (e.g., handles 62, 80, etc.) provide a modular system that may be used with syringe barrels 20A, 20B, 20C, 20D (which may, e.g., be configured as barrel 20, 20', etc.) of a variety of different configurations, as shown in FIG. 9. By way of example only, barrels of a plurality of different volumes, of a plurality of different dimensions, that include a plurality of different optional features (e.g., no optional features, release valves, ports configured for connection to pressure gauges and other apparatus, inlet ports, etc.), or the like may be used with one reusable handle. Of course, differently configured syringe barrels that are configured for use with the same rotatable element may have commonly dimensioned features for engagement by the rotatable element, or may be used in combination with adapters that facilitate their use with the same rotatable element.

Figure 10:
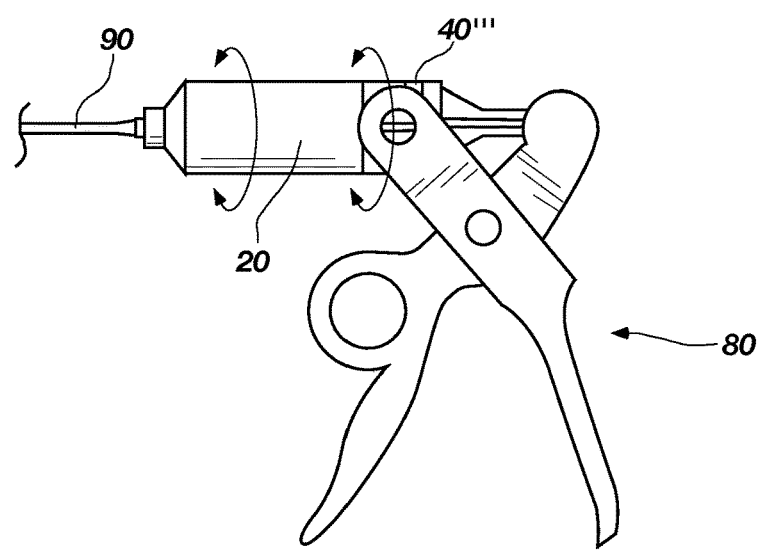
FIG. 10 is a schematic view of a system including a syringe with a rotatable element around a syringe barrel and an infusion/aspiration element secured to a distal end of the syringe barrel.

Referring now to FIG. 10, in use, a rotatable element that incorporates teachings of the present invention (e.g., rotatable element 40, 40", 40'", etc.) allows for some movement of syringe handles (e.g., handle 62, handle 80, etc.) while the barrel (e.g., barrel 20, 20', etc.) and a distally located peripheral device 90, such as a catheter or needle, remains substantially stationary. Thus, a syringe according to the present invention eliminates the need for relatively complex and expensive rotatable fittings, or coupling elements, such as slip ring leur locks.

In addition to being able to rotate about a barrel (e.g., barrel 20 or 20), a rotatable element (e.g., rotatable element 40, 40", 40'", etc.) that embodies teachings of the present invention enables the barrel to rotate as the rotatable element is held (e.g., by a handle 62, 80, etc.) in a stationary or somewhat stationary (accounting for normal movement by a healthcare provider operating the handle) position. This feature may be useful for coupling a syringe of the present invention to a distally located peripheral device that is already in place in a subject's body.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed:

1. A syringe comprising:
   a barrel that comprises:
      a distal end having a distal tip;
      a proximal end opposite from the distal end;
      an axle circumferentially recessed relative to an outer surface of the barrel and located at the proximal end of the barrel;
      a receptacle defined in and extending axially through the barrel; and
      a retention feature capable of preventing removal of a rotatable element from the axle;
   a plunger, a distal end of which is disposed in the receptacle within the barrel and a proximal end of which extends from the proximal end of the barrel;
   the rotatable element positioned over the axle of the barrel and extending over only a portion of a length of the barrel, a proximal ridge adjacent to the axle capable of retaining the rotatable element on an exterior of the barrel to prevent distal movement of the rotatable element along the barrel while enabling the rotatable element to spin around the axle of the barrel, the rotatable element being located between the retention feature of the barrel and the distal end of the barrel; and
   a handle protruding from the rotatable element.

2. The syringe of claim 1, wherein the rotatable element is positioned between the proximal ridge and a locking element located on opposite sides of the axle.

3. The syringe of claim 1, wherein the axle comprises a single circumferential protrusion having an annular shape, the single circumferential protrusion engaging a single groove formed in an inner surface of the rotatable element.

4. The syringe of claim 1, wherein the syringe is capable of substantially preventing movement of the rotatable element toward and away from each of the proximal and distal ends of the barrel without preventing rotation of the rotatable element about the axle.

5. The syringe of claim 1, wherein the retention feature is located between the rotatable element and the proximal end of the barrel.

6. The syringe of claim 1, further comprising:
   a locking element disposed on the barrel toward the proximal end thereof and capable of retaining the rotatable element on the axle.

7. The syringe of claim 6, wherein the axle is also circumferentially recessed relative to an outer surface of the locking element.

8. The syringe of claim 1, wherein the handle comprises finger loops.

9. The syringe of claim 8, wherein the proximal end of the plunger comprises a thumb loop.

10. The syringe of claim 1, wherein the rotatable element comprises a pair of axially aligned hinge elements protruding therefrom.

11. The syringe of claim 10, wherein the handle comprises a syringe actuation handle that includes a pair of members that are pivotally associated with one another, one of the members being pivotally coupled to the axially aligned hinge elements of the rotatable element, and another of the members being pivotally coupled to the plunger.

12. A syringe comprising:
    a barrel that comprises:
       a distal tip;
       a proximal end opposite from the distal tip;
       the proximal end comprising an axle at an outer surface of the barrel;
       a wall defining a receptacle that extends axially through the barrel; and
       a retention feature capable of preventing removal of a rotatable element from the axle;
    the rotatable element disposed around the axle of the barrel and extending over only a portion of a length of the barrel, a proximal ridge adjacent to the axle capable of preventing distal movement of the rotatable element while enabling the rotatable element to spin around the axle of the barrel, the retention feature of the barrel being located between the rotatable element and the proximal end of the barrel; and
    a handle protruding from the rotatable element.

13. The syringe of claim 12, further comprising a plunger partially disposed in the receptacle and extending out of the proximal end of the barrel.

14. The syringe of claim 12, wherein the barrel includes a first outer diameter and a second outer diameter smaller than the first outer diameter defining the axle, and wherein the rotatable element is disposed about the second outer diameter.

15. The syringe of claim 12, wherein the axle comprises a single circumferential protrusion having an annular shape, the single circumferential protrusion engaging a single groove formed in an inner surface of the rotatable element.

16. The syringe of claim 12, wherein the syringe is capable of substantially preventing movement of the rotatable element toward and away from the proximal end and the distal tip of the barrel without preventing rotation of the rotatable element about the axle.

17. The syringe of claim 12, wherein the rotatable element is located between the retention feature and the distal tip of the barrel.

18. The syringe of claim 12, further comprising:
    a locking element disposed on the barrel toward the proximal end thereof and capable of retaining the rotatable element on the axle.

19. The syringe of claim 18, wherein the axle is circumferentially recessed relative to an outer surface of a main body of the barrel and relative to an outer surface of the locking element.

20. The syringe of claim 12, wherein the handle comprises finger loops that protrude from the rotatable element.

21. The syringe of claim 20, further comprising:
    a plunger, a distal end of which is disposed in the receptacle within the barrel and a proximal end of which extends out from the proximal end of the barrel, wherein the proximal end of the plunger comprises a thumb loop.

22. The syringe of claim 12, wherein the rotatable element comprises a pair of axially aligned hinge elements protruding therefrom.

23. The syringe of claim 22, wherein the handle includes a pair of members pivotally associated with one another, one of the members being pivotally coupled to the hinge elements, and another of the members being pivotally coupled to a plunger.

\* \* \* \* \*